(12) United States Patent
Sinha et al.

(10) Patent No.: US 9,079,864 B2
(45) Date of Patent: Jul. 14, 2015

(54) MODULATORS OF S1P RECEPTORS

(75) Inventors: Santosh C. Sinha, Ladera Ranch, CA (US); Smita S. Bhat, Irvine, CA (US); Ken Chow, Newport Coast, CA (US); Michael E. Garst, Newport Beach, CA (US); Wha Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 276 days.

(21) Appl. No.: 13/293,768

(22) Filed: Nov. 10, 2011

(65) Prior Publication Data

US 2012/0129906 A1    May 24, 2012

Related U.S. Application Data

(60) Provisional application No. 61/416,939, filed on Nov. 24, 2010.

(51) Int. Cl.
| C07D 233/64 | (2006.01) |
| A61K 31/4164 | (2006.01) |
| C07D 233/61 | (2006.01) |
| C07D 233/60 | (2006.01) |

(52) U.S. Cl.
CPC ............ C07D 233/61 (2013.01); C07D 233/60 (2013.01)

(58) Field of Classification Search
CPC .......................... C07D 233/64; A61K 31/4164
USPC .............................. 548/316.4, 336.1; 514/396
See application file for complete search history.

(56) References Cited

U.S. PATENT DOCUMENTS 5,965,743 A * 10/1999 Mochizuki et al. ........ 548/335.5
2001/0044445 A1    11/2001  Bamaung

FOREIGN PATENT DOCUMENTS

| EP | 0757988 | 2/1997 |
| EP | 1760071 | 3/2007 |
| EP | 1860098 | 11/2007 |
| JP | 2001139575 | 5/2001 |
| SU | 477157 | 7/1975 |
| WO | 00-76489 | 12/2000 |
| WO | 02-18361 | 3/2002 |
| WO | 2008-049047 | 4/2008 |
| WO | 2008-100618 | 8/2008 |
| WO | WO 2009-038759 | 3/2009 |
| WO | 2010-100475 | 9/2010 |
| WO | 2011-044073 | 4/2011 |
| WO | 2011-092140 | 8/2011 |

OTHER PUBLICATIONS

STN/CAS search results for US Patent 6,252,090, Vasudevan et al., 2001.*
Matsunaga et al. Bioorg. Med. Chem. 12 (2004) 2251-2273.*
Cross, L.C. et al., Rules for the Nomencalture of Organic Chemistry Section E: Stereochemistry, Pure Appli. Chem. (1976), 45, 11-30.
Stahl, Heinrich et al., Handbook of Pharmaceutical Salts, Verlag Helvetica Chimica Acta—Zurich, 2002, 329-345.

* cited by examiner

Primary Examiner — Yong Chu
Assistant Examiner — Sonya Wright
(74) Attorney, Agent, or Firm — Barbara C. Potts

(57) ABSTRACT

The present invention relates to novel diphenylethyne derivatives, processes for preparing them, pharmaceutical compositions containing them and their use as pharmaceuticals as modulators of sphingosine-1-phosphate receptors.

6 Claims, No Drawings

MODULATORS OF S1P RECEPTORS

CROSS REFERENCE TO RELATED APPLICATIONS

This application claims the benefit of U.S. Provisional Application Ser. No. 61/416,939 filed Nov. 24, 2010, which is hereby incorporated by reference in its entirety.

FIELD OF THE INVENTION

The present invention relates to novel diphenylethyne derivatives, processes for preparing them, pharmaceutical compositions containing them and their use as pharmaceuticals, as modulators of sphingosine-1-phosphate receptors. The invention relates specifically to the use of these compounds and their pharmaceutical compositions to treat disorders associated with sphingosine-1-phosphate 1 (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

A group of diphenylethyne derivatives, which are potent and selective sphingosine-1-phosphate modulators has been discovered. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This document describes compounds of Formula I, which have sphingosine-1-phosphate receptor biological activity. The compounds in accordance with the present invention are thus of use in medicine, for example in the treatment of humans with diseases and conditions that are alleviated by S1P modulation. In an embodiment, the invention provides a compound having Formula I or individual stereoisomeric forms thereof, or individual geometrical isomers, or individual enantiomers, or individual diastereoisomers, or individual tautomers, or individual zwitterions or a pharmaceutically acceptable salt thereof:

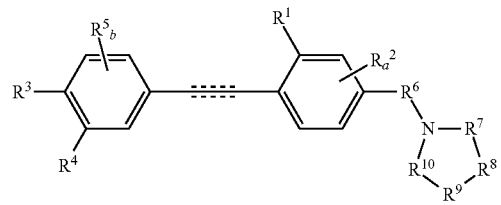

Formula I wherein:

" ===== " represents a single bond "—$CH_2$—$CH_2$—" or a double bond "—CH=CH—" or a triple bond "—C≡C—";

$R^1$ is H, halogen, —$OC_{1-3}$ alkyl, $C_{1-8}$ alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^2$ is the same or independently halogen, —$OC_{1-3}$ alkyl, $C_{1-8}$ alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^3$ is H, halogen, —$OC_{1-3}$ alkyl, $C_{1-8}$alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^4$ is H, halogen, —$OC_{1-3}$ alkyl, $C_{1-8}$alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^5$ is the same or independently halogen, —$OC_{1-3}$ alkyl, $C_{1-8}$alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^6$ is O, $NR^{14}$, S, S(=O), S(=O)$_2$, S(=O)$_2NR^{15}$, $CR^{16}R^{17}$, C=O, C=S or direct bond;

$R^7$ is O, S, $NR^{18}$, $CR^{19}R^{20}$ or forms together with $R^8$ a HC=CH double bond or a HC=N double bond or a N=CH double bond;

$R^8$ is O, S, $NR^{18}$, $CR^{19}R^{20}$ or forms together with $R^7$ a HC=CH double bond or a HC=N double bond or a N=CH double bond;

$R^9$ is O, S, $NR^{18}$, $CR^{19}R^{20}$ or forms together with $R^{10}$ a HC=CH double bond or a HC=N double bond or a N=CH double bond;

$R^{10}$ is O, S, $NR^{18}$, $CR^{19}R^{20}$ or forms together with $R^9$ a HC=CH double bond or a HC=N double bond or a N=CH double bond;

$R^{11}$ is H, $C_{3-8}$ cycloalkyl, $C_{3-10}$ cycloalkenyl, $C_{6-10}$ aryl, heterocycle, or $C_{1-5}$ alkyl;

$R^{12}$ is H, $C_{3-8}$ cycloalkyl, $C_{3-10}$ cycloalkenyl, $C_{6-10}$ aryl, heterocycle, or $C_{1-5}$ alkyl;

$R^{13}$ is H, $C_{3-8}$ cycloalkyl, $C_{3-10}$ cycloalkenyl, $C_{6-10}$ aryl, heterocycle, or $C_{1-5}$ alkyl;

$R^{14}$ is H, $C_{3-8}$ cycloalkyl, $C_{3-10}$ cycloalkenyl, $C_{6-10}$ aryl, heterocycle, or $C_{1-5}$ alkyl;

$R^{15}$ is H or $C_{1-8}$alkyl;

$R^{16}$ is H, halogen or $C_{1-8}$alkyl;

$R^{17}$ is H, halogen or $C_{1-8}$alkyl;

$R^{18}$ is is H, halogen $C_{3-8}$ cycloalkyl, $C_{3-10}$ cycloalkenyl, $C_{6-10}$ aryl, heterocycle or $C_{1-8}$alkyl;

$R^{19}$ is H, halogen, $C_{3-8}$ cycloalkyl, $C_{3-10}$ cycloalkenyl, $C_{6-10}$ aryl, heterocycle or $C_{1-8}$alkyl;

$R^{20}$ is H, halogen, $C_{3-8}$ cycloalkyl, $C_{3-10}$ cycloalkenyl, $C_{6-10}$ aryl, heterocycle or $C_{1-8}$alkyl;

a is 0, 1, 2 or 3; and b is 0, 1, 2 or 3.

In a further embodiment, the invention provides a compound having Formula I, wherein:

"======" represents a triple bond "—C≡C—";

$R^1$ is H, halogen, —$OC_{1-3}$ alkyl, $C_{1-8}$ alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^2$ is independently halogen, —$OC_{1-3}$ alkyl, $C_{1-8}$ alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^3$ is H, halogen, —$OC_{1-3}$ alkyl, $C_{1-8}$ alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^4$ is H, halogen, —$OC_{1-3}$ alkyl, $C_{1-8}$ alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^5$ is independently halogen, —$OC_{1-3}$ alkyl, $C_{1-8}$ alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^6$ is O, $NR^{14}$, S, $S(=O)$, $S(=O)_2$, $S(=O)_2NR^{15}$, $CR^{16}R^{17}$, C=O, C=S or direct bond;

$R^7$ is O, S, $NR^{18}$, $CR^{19}R^{20}$ or forms together with $R^8$ a HC=CH double bond or a HC=N double bond or a N=CH double bond;

$R^8$ is O, S, $NR^{18}$, $CR^{19}R^{20}$ or forms together with $R^7$ a HC=CH double bond or a HC=N double bond or a N=CH double bond;

$R^9$ is O, S, $NR^{18}$, $CR^{19}R^{20}$ or forms together with $R^{10}$ a HC=CH double bond or a HC=N double bond or a N=CH double bond;

$R^{10}$ is O, S, $NR^{18}$, $CR^{19}R^{20}$ or forms together with $R^9$ a HC=CH double bond or a HC=N double bond or a N=CH double bond;

$R^{11}$ is H, $C_{3-8}$ cycloalkyl, $C_{3-10}$ cycloalkenyl, $C_{6-10}$ aryl, heterocycle, or $C_{1-5}$ alkyl;

$R^{12}$ is H, $C_{3-8}$ cycloalkyl, $C_{3-10}$ cycloalkenyl, $C_{6-10}$ aryl, heterocycle, or $C_{1-5}$ alkyl;

$R^{13}$ is H, $C_{3-8}$ cycloalkyl, $C_{3-10}$ cycloalkenyl, $C_{6-10}$ aryl, heterocycle, or $C_{1-5}$ alkyl;

$R^{14}$ is H, $C_{3-8}$ cycloalkyl, $C_{3-10}$ cycloalkenyl, $C_{6-10}$ aryl, heterocycle, or $C_{1-5}$ alkyl;

$R^{15}$ is H or $C_{1-8}$ alkyl;

$R^{16}$ is H, halogen or $C_{1-8}$ alkyl;

$R^{17}$ is H, halogen or $C_{1-8}$ alkyl;

$R^{18}$ is H, halogen $C_{3-8}$ cycloalkyl, $C_{3-10}$ cycloalkenyl, $C_{6-10}$ aryl, heterocycle or $C_{1-8}$ alkyl;

$R^{19}$ is H, halogen, $C_{3-8}$ cycloalkyl, $C_{3-10}$ cycloalkenyl, $C_{6-10}$ aryl, heterocycle or $C_{1-8}$ alkyl;

$R^{20}$ is H, halogen, $C_{3-8}$ cycloalkyl, $C_{3-10}$ cycloalkenyl, $C_{6-10}$ aryl, heterocycle or $C_{1-8}$ alkyl;

a is 0, 1, 2 or 3; and b is 0, 1, 2 or 3.

In a further embodiment, the invention provides a compound having Formula I wherein:

"======" represents a single bond "—$CH_2$—$CH_2$—".

In a further embodiment, the invention provides a compound having Formula I wherein:

"======" represents a double bond "—CH=CH—".

In a further embodiment, the invention provides a compound having Formula I wherein:

"======" represents a triple bond "—C≡C—";

$R^1$ is H, halogen or $C_{1-8}$ alkyl;

$R^2$ is independently halogen, —$OC_{1-3}$ alkyl, $C_{1-8}$ alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^3$ is —$OC_{1-3}$ alkyl;

$R^4$ is H, halogen, $C_{1-8}$ alkyl or CN;

$R^5$ is independently halogen, —$OC_{1-3}$ alkyl, $C_{1-8}$ alkyl, CN, $C(O)R^{11}$, $C_{3-8}$ cycloalkyl, $C_{3-10}$ cycloalkenyl, $C_{6-10}$ aryl, heterocycle, $NR^{12}R^{13}$ or hydroxyl;

$R^6$ is $CR^{16}R^{17}$;

$R^7$ is $CR^{19}R^{20}$ or forms together with $R^8$ a HC=CH double bond or a HC=N double bond or a N=CH double bond;

$R^8$ is $CR^{19}R^{20}$ or forms together with $R^7$ a HC=CH double bond or a HC=N double bond or a N=CH double bond;

$R^9$ is $CR^{19}R^{20}$ or forms together with $R^{10}$ a HC=CH double bond or a HC=N double bond or a N=CH double bond;

$R^{10}$ is $CR^{19}R^{20}$ or forms together with $R^9$ a HC=CH double bond or a HC=N double bond or a N=CH double bond;

$R^{11}$ is H, $C_{3-8}$ cycloalkyl, $C_{3-10}$ cycloalkenyl, $C_{6-10}$ aryl, heterocycle, or $C_{1-5}$ alkyl;

$R^{12}$ is H, $C_{3-8}$ cycloalkyl, $C_{3-10}$ cycloalkenyl, $C_{6-10}$ aryl, heterocycle, or $C_{1-5}$ alkyl;

$R^{13}$ is H, $C_{3-8}$ cycloalkyl, $C_{3-10}$ cycloalkenyl, $C_{6-10}$ aryl, heterocycle, or $C_{1-5}$ alkyl;

$R^{16}$ is H;

$R^{17}$ is H;

$R^{19}$ is H;

$R^{20}$ is H;

a is 0, 1, 2 or 3; and b is 0, 1, 2 or 3.

In a further embodiment, the invention provides a compound having Formula I wherein:

"======" represents a triple bond "—C≡C—";

$R^1$ is H, halogen or $C_{1-8}$ alkyl;

$R^3$ is —$OC_{1-3}$ alkyl;

$R^4$ is H, halogen, —$C_{1-8}$ alkyl or CN;

$R^6$ is $CR^{16}R^{17}$;

$R^7$ is $CR^{19}R^{20}$ or forms together with $R^8$ a HC=CH double bond or a HC=N double bond or a N=CH double bond;

$R^8$ is $CR^{19}R^{20}$ or forms together with $R^7$ a HC=CH double bond or a HC=N double bond or a N=CH double bond;

$R^9$ is $CR^{19}R^{20}$ or forms together with $R^{10}$ a HC=CH double bond or a HC=N double bond or a N=CH double bond;

$R^{10}$ is $CR^{19}R^{20}$ or forms together with $R^9$ a HC=CH double bond or a HC=N double bond or a N=CH double bond;

$R^{16}$ is H;

$R^{17}$ is H;

$R^{19}$ is H;

$R^{20}$ is H;

a is 0; and b is 0.

In a further embodiment, the invention provides a compound having Formula I wherein:

"======" represents a triple bond "—C≡C—";

$R^1$ is H, halogen or $C_{1-8}$ alkyl;

$R^3$ is —$OC_{1-3}$ alkyl;

$R^4$ is H, halogen, —$C_{1-8}$ alkyl or CN;

$R^6$ is $CR^{16}R^{17}$;

$R^7$ is $CR^{19}R^{20}$;

$R^8$ is $CR^{19}R^{20}$;

$R^9$ is $CR^{19}R^{20}$;

$R^{10}$ is $CR^{19}R^{20}$;

$R^{16}$ is H;

$R^{17}$ is H;

$R^{19}$ is H;

$R^{20}$ is H;

a is 0; and b is 0.

In a further embodiment, the invention provides a compound having Formula I wherein:
"======" represents a triple bond "—C≡C—";
$R^1$ is H, halogen or $C_{1-8}$alkyl;
$R^3$ is —O(iso-propyl);
$R^4$ is H, halogen, —$C_{1-8}$alkyl or CN;
$R^6$ is $CR^{16}R^{17}$;
$R^7$ is $CR^{19}R^{20}$;
$R^8$ is $CR^{19}R^{20}$;
$R^9$ is $CR^{19}R^{20}$;
$R^1$ is $CR^{19}R^{20}$;
$R^{16}$ is H;
$R^{17}$ is H;
$R^{19}$ is H;
$R^{29}$ is H;
a is 0; and
b is 0.

In a further embodiment, the invention provides a compound having Formula I wherein:
"======" represents a triple bond "—C≡C—";
$R^1$ is H, halogen or $C_{1-8}$alkyl;
$R^3$ is —$OC_{1-3}$ alkyl;
$R^4$ is H, halogen, —$C_{1-8}$alkyl or CN;
$R^6$ is $CR^{16}R^{17}$;
$R^7$ forms together with $R^8$ a HC=N double bond;
$R^9$ forms together with $R^{10}$ a HC=CH double bond;
$R^{16}$ is H;
$R^{17}$ is H;
a is 0; and
b is 0.

In a further embodiment, the invention provides a compound having Formula I wherein:
"======" represents a triple bond "—C≡C—";
$R^1$ is H, halogen or $C_{1-8}$alkyl;
$R^3$ is —O(iso-propyl);
$R^4$ is H, halogen, —$C_{1-8}$alkyl or CN;
$R^6$ is $CR^{16}R^{17}$;
$R^7$ forms together with $R^8$ a HC=N double bond;
$R^9$ forms together with $R^{10}$ a HC=CH double bond;
$R^{16}$ is H;
$R^{17}$ is H;
a is 0; and
b is 0.

In a further embodiment, the invention provides a compound having Formula I wherein:
"======" represents a triple bond "—C≡C—".
$R^1$ is H, halogen or $C_{1-8}$alkyl;
$R^3$ is —$OC_{1-3}$ alkyl;
$R^4$ is H, halogen, —$C_{1-8}$alkyl or CN;
$R^6$ is $CR^{16}R^{17}$;
$R^7$ forms together with $R^8$ a HC=CH double bond;
$R^{10}$ forms together with $R^9$ a HC=N double bond;
$R^{16}$ is H;
$R^{17}$ is H;
a is 0; and
b is 0.

In a further embodiment, the invention provides a compound having Formula I wherein:
"======" represents a triple bond "—C≡C—".
$R^1$ is H, halogen or $C_{1-8}$alkyl;
$R^3$ is —O(iso-propyl);
$R^4$ is H, halogen, —$C_{1-8}$alkyl or CN;
$R^6$ is $CR^{16}R^{17}$;
$R^7$ forms together with $R^8$ a HC=CH double bond;
$R^{10}$ forms together with $R^9$ a HC=N double bond;
$R^{16}$ is H;
$R^{17}$ is H;
a is 0; and
b is 0.

The term "alkyl", as used herein, refers to saturated, monovalent hydrocarbon moieties having linear or branched moieties or combinations thereof and containing 1-8 carbon atoms, unless otherwise specified. One methylene (—$CH_2$—) group, of the alkyl group can be replaced by oxygen, sulfur, sulfoxide, nitrogen, carbonyl, carboxyl, sulfonyl, phosphate or by a divalent $C_{3-6}$ cycloalkyl. Alkyl moieties can optionally be substituted by halogen atoms, hydroxyl groups, cycloalkyl groups, amino groups, heterocycle groups, carboxylic acid groups, phosphonic acid groups, sulphonic acid groups, phosphoric acid groups.

The term "—$OC_{1-3}$ alkyl", as used herein, refers to a monovalent moiety having an oxygen atom linked to a $C_{1-3}$ alkyl group, as defined above, and linked to the rest of the molecule.

The term "cycloalkenyl", as used herein, refers to a monovalent or divalent group of 3 to 10 carbon atoms derived from a saturated cycloalkyl having one double bond. Cycloalkenyl groups can be monocyclic or polycyclic. Cycloalkenyl groups can be substituted by alkyl groups or halogen atoms.

The term "cycloalkyl", as used herein, refers to a monovalent or divalent group of 3 to 8 carbon atoms, derived from a saturated cyclic hydrocarbon. Cycloalkyl can be optionally substituted by $C_{1-3}$ alkyl groups or halogen atoms.

The term "halogen", as used herein, refers to an atom of chlorine, bromine, fluorine, iodine.

The term "heterocycle" as used herein, refers to a 3 to 10 membered ring, containing at least one heteroatom selected form O or N or S or combinations of at least two thereof interrupting the carbocyclic ring structure. The heterocyclic ring can be saturated or non-saturated. The heterocyclic ring can be interrupted by a C=O, the S heteroatom can be oxidized. Heterocyclic ring moieties can optionally be substituted by hydroxyl groups, $C_{1-3}$ alkyl groups or halogen atoms. Heterocycles can be monocyclic or polycyclic.

The term "aryl" as used herein, is defined as including an organic moiety derived from an aromatic hydrocarbon consisting of a ring containing 6 to 10 carbon atoms by removal of one hydrogen. Aryl can optionally be substituted by halogen atoms or by $C_{1-3}$ alkyl groups. Aryl can be monocyclic or polycyclic.

The term "amide" as used herein, represents a group of formula "—C(O)$NH_2$".

The term "hydroxyl" as used herein, represents a group of formula "—OH".

The term "carbonyl" as used herein, represents a group of formula "—C=O".

The term "carboxyl" as used herein, represents a group of formula "—C(O)O—".

The term "cyano" as used herein, represents a group of formula "—CN".

The term "aldehyde" as used herein, represents a group of formula "—C(O)H".

The term "sulfate" as used herein, represents a group of formula "—$SO_2$".

The term "sulfonyl" as used herein, represents a group of formula "—O—S(O)$_2$—O—".

The term "carboxylic acid" as used herein, represents a group of formula "—C(O)OH".

The term "sulfoxide" as used herein, represents a group of formula "—S=O".

The term "phosphate" as used herein, represents a group of formula "—P(O)(OH)$_2$".

The term "phosphoric acid" as used herein, represents a group of formula "—(O)P(O)(OH)$_2$".

The term "sulphonic acid" as used herein, represents a group of formula "—S(O)$_2$OH".

Some compounds of the invention are:

5-{[4-(1H-imidazol-1-ylmethyl)phenyl]ethynyl}-2-isopropoxybenzonitrile;

5-{[4-(1H-imidazol-1-ylmethyl)-2-methylphenyl]ethynyl}-2-isopropoxybenzonitrile;

1-[4-(3-Chloro-4-isopropoxy-phenylethynyl)-benzyl]-1H-imidazole;

2-isopropoxy-5-{[4-(pyrrolidin-1-ylmethyl)phenyl] ethynyl}benzonitrile;

5-{[2-chloro-4-(1H-imidazol-1-ylmethyl)phenyl]ethynyl}-2-isopropoxybenzonitrile;

1-{4-[(3-bromo-4-isopropoxyphenyl)ethynyl]benzyl}-1H-imidazole;

1-[4-(3-Methyl-4-isopropoxy-phenylethynyl)-benzyl]-1H-imidazole.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahl & Camille G. Wermuth (Eds), Verlag Helvetica Chimica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation.

Therapeutic utilities of S1P modulators are:

Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immnuosuppression: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for therapeutic utilities of S1P modulators:

Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immunosuppression: rheumatoid arthritis, Crohn's disease, Graves' disease, inflammatory bowel disease, multiple sclerosis, Myasthenia gravis, Psoriasis, ulcerative colitis, autoimmune uveitis, renal ischemia/perfusion injury, contact hypersensitivity, atopic dermatitis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of Formula I according to the invention can be prepared analogously to conventional methods as understood by the person skilled in the art of synthetic organic chemistry. The synthetic scheme set forth below, illustrate how compounds according to the invention can be made.

The following abbreviations are used in the general schemes and in the examples:
DCM or $CH_2Cl_2$ dichloromethane
$CDCl_3$ deuterated chloroform
MeOH methanol
$CD_3OD$ deuterated methanol
DMF N,N dimethylformamide
THF tetrahydrofuran
$CH_3CN$ acetonitrile
$MgSO_4$ magnesium sulfate
MPLC medium pressure column chromatography
CuI copper iodide
r.t. room temperature
$K_2CO_3$ potassium carbonate
DIPEA N,N-Diisopropylethylamine
$Et_3N$ triethylamine
$SOCl_2$ thionylchloride Scheme 1

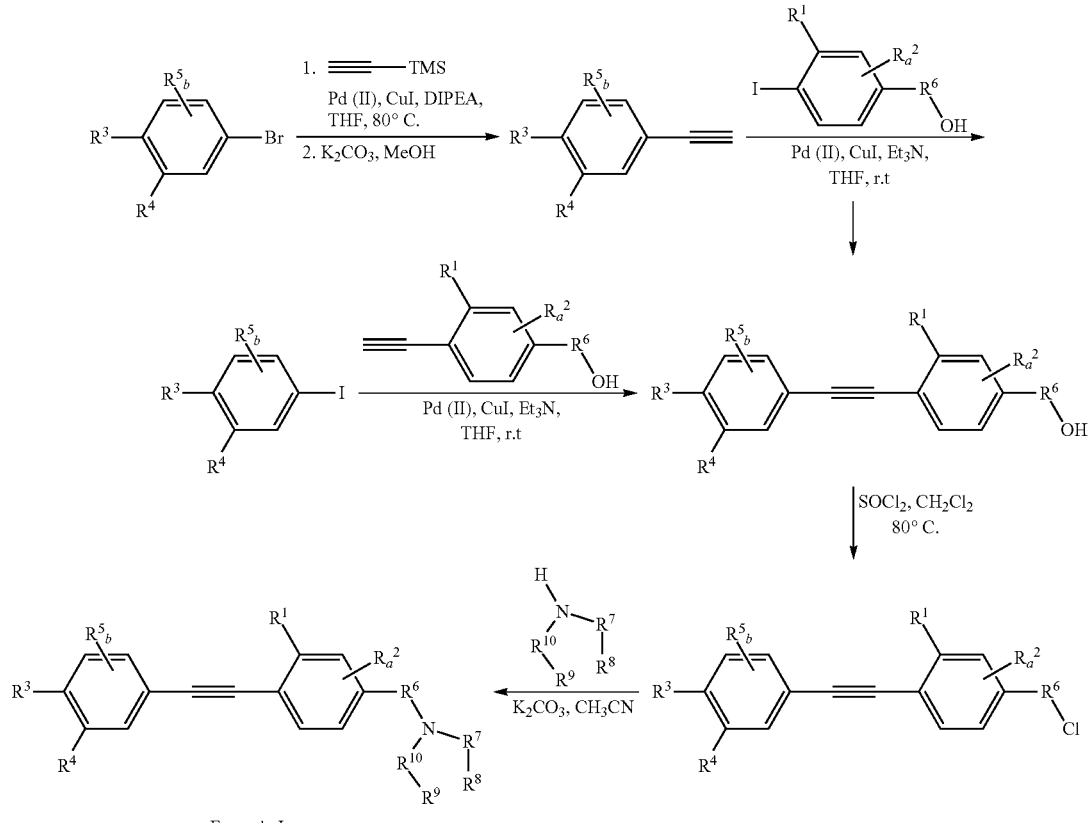

Formula I

A solution of a bromo aryl in tetrahydrofuran was treated with copper (I) iodide and then purged with Argon for 5 minutes. A trimethyl silyl acetylene derivative was added followed by dichlorobis-(triphenylphosphine)palladium(II). The resultant mixture was heated at 80° C. overnight in a sealed tube. The mixture was evaporated and purified by column chromatography to give the corresponding trimethylsilylethynyl intermediate. The trimethylsilylethynyl intermediate dissolved in methanol was treated with potassium carbonate at room temperature overnight.

The reaction mixture was filtered and the filtrate was evaporated to give the crude product, which was purified on a column (MPLC) using hexane:ethyl acetate. The alkyne derivative in tetrahydrofuran was treated with copper (I) iodide then purged with Argon for 5 minutes.

The iodophenylmethanol derivative was added followed by dichlorobis-(triphenylphosphine)palladium(II). The resultant mixture was heated at 80° C. overnight. The reaction was filtered and the filtrate was evaporated to give the crude product. The crude product was purified on a column (MPLC) using hexane:ethyl acetate to afford the hydroxyl alkyne intermediate. The hydroxyl alkyne intermediate can also be obtained from the (4-ethynylphenyl)methanol derivative. The methanol derivative was dissolved in tetrahydrofuran then treated with copper (I) iodide and purged with Argon for 5 minutes. A substituted iodophenyl derivative was added followed by addition of dichlorobis-(triphenylphosphine)palladium(II). The resultant mixture was heated at 80° C. overnight. The reaction was filtered and the filtrate was evaporated to give the corresponding hydroxyl alkyne intermediate.

The hydroxyl alkyne intermediate dissolved in dichloromethane was treated with thionyl chloride and the reaction was heated at 80° C. for 1 h. The reaction mixture was cooled at room temperature; the solvent evaporated and the residue was washed with ether several times to afford the corresponding chloro alkyne intermediate.

The chloro alkyne intermediate, imidazole and potassium carbonate were stirred at reflux in acetonitrile overnight. The solution was cooled at room temperature, then diluted with dichloromethane and washed with water. The organic phase was washed with brine, dried over (MgSO$_4$), filtered, and concentrated under reduced pressure. Purification by column chromatography (2% MeOH in CH$_2$Cl$_2$) gave the desired product of Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

The IUPAC names of the compounds mentioned in the examples were generated with ACD version 8 and intermediates and reagent names used in the examples were generated with software such as Chem Bio Draw Ultra version 12.0 or Auto Nom 2000 from MDL ISIS Draw 2.5 SP1.

Unless specified otherwise in the examples, characterization of the compounds is performed with NMR spectra which are recorded on 300 or 600 MHz Varian and acquired at room temperature. Chemical shifts are given in ppm referenced either to internal trimethylsilyl or to the residual solvent signal.

All the reagents, solvents, catalysts for which the synthesis is not described are purchased from chemical vendors such as Sigma Aldrich, Fluka, Bio-Blocks, Ryan Scientific, Syn Chem, Chem-Impex, Aces Pharma, however some known intermediates, for which the CAS registry number [CAS #] are mentioned, were prepared in-house following known procedures.

Usually the compounds of the invention were purified by flash column chromatography using a gradient solvent system of methanol/dichloromethane unless otherwise reported.

EXAMPLE 1

Intermediate 1

5-ethynyl-2-isopropoxybenzonitrile

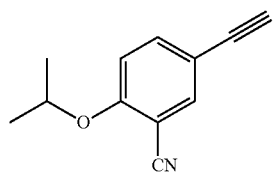

A solution of 5-bromo-2-isopropoxybenzonitrile (1.0 g, 4.16 mmol) in tetrahydrofuran was treated with copper (I) iodide (0.158 g, 0.83 mmol) and then purged with Argon for 5 minutes. Trimethyl silyl acetylene (2.85 g, 29.16 mmol) was then added followed by dichlorobis-(triphenylphosphine)palladium(II) (0.291 g, 0.41 mmol). The resultant mixture was heated at 80° C. overnight in a sealed tube. The mixture was evaporated and purified by column chromatography to give 2-isopropoxy-5-((trimethylsilyl)ethynyl)benzonitrile which was taken to the next step. 2-isopropoxy-5-((trimethylsilyl)

ethynyl)benzonitrile (1.0 g, 3.8 mmol) in methanol (20 mL) was treated with potassium carbonate (1.07 g, 7.7 mmol) at room temperature overnight. The reaction was filtered and the filtrate was evaporated to give the crude product. The crude product was purified on a column (MPLC) using hexane:ethyl acetate and afforded Intermediate 1.

¹H-NMR (CDCl₃, 300 MHz) δ=7.94 (s, 1H), 7.66 (d, J=8.7 Hz, 1H), 7.61 (d, J=8.7 Hz, 1H), 4.62-4.70 (m, 1H), 1.42 (s, 3H), 1.41 (s, 3H).

EXAMPLE 2

Intermediate 2

5-{[4-(hydroxymethyl)phenyl]ethynyl}-2-isopropoxybenzonitrile

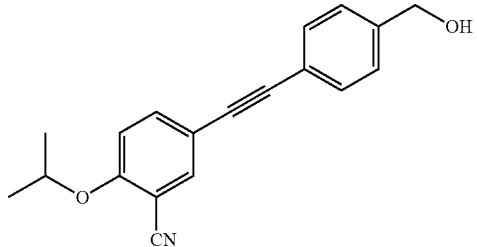 [SMILES: CC(C)Oc1ccc(C#Cc2ccc(CO)cc2)cc1C#N]

Intermediate 1 (300 mgs, 1.8 mmol) in THF was treated with copper (I) iodide (6 mgs, 0.03 mmol) and then purged with Argon for 5 minutes. (4-iodophenyl)methanol (413 mgs, 1.8 mmol), was then added followed by dichlorobis-(triphenylphosphine)palladium(II) (11 mgs, 0.016 mmol). The resulting mixture was heated at 80° C. overnight. The reaction was filtered and the filtrate was evaporated to give the crude product. The crude product was purified on a column (medium pressure liquid chromatography) using hexane:ethyl acetate and afforded Intermediate 2.

¹H-NMR (CDCl₃, 300 MHz) δ=7.66 (s, 1H), 7.51 (d, J=8.1 Hz, 2H), 7.34 (d, J=8.1 Hz, 2H), 7.21 (s, 1H), 6.74 (d, J=8.7 Hz, 1H), 4.75 (s, 2H), 4.60-4.75 (m, 1H), 1.42 (s, 3H), 1.40 (s, 3H).

EXAMPLE 3

Intermediate 3

5-{[4-(chloromethyl)phenyl]ethynyl}-2-isopropoxybenzonitrile

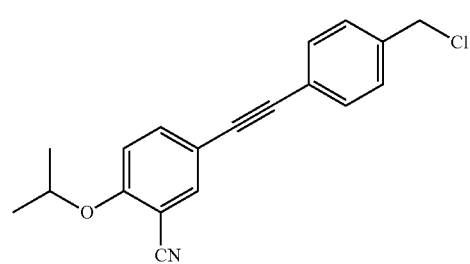 [SMILES: CC(C)Oc1ccc(C#Cc2ccc(CCl)cc2)cc1C#N]

Intermediate 2 (400 mgs, 1.37 mmol) in CH₂Cl₂ was treated with thionyl chloride (240 mgs, 2.06 mmol) and the reaction was heated at 80° C. for 1 h. The reaction mixture was cooled at room temperature. The solvent was evaporated and the residue was washed with ether several times and afforded Intermediate 3.

¹H-NMR (CDCl₃, 300 MHz) δ=7.86 (s, 1H), 7.60 (d, J=8.7 Hz, 2H), 7.64 (d, J=8.7 Hz, 2H), 7.33 (s, 1H), 6.54 (d, J=8.7 Hz, 1H), 4.58 (s, 2H), 4.62-4.75 (m, 1H), 1.43 (s, 3H), 1.40 (s, 3H).

EXAMPLE 4

Intermediate 4

(4-((4-isopropoxy-3-methylphenyl)ethynyl)phenyl)methanol

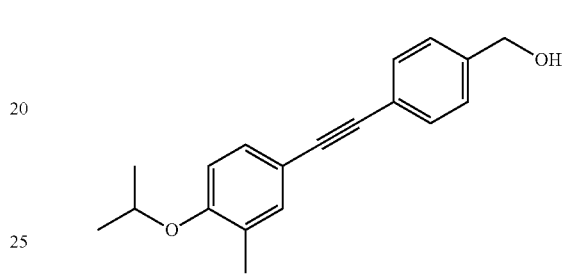

A solution of (4-ethynylphenyl)methanol (CAS 10602-04-7) (250 mgs, 1.9 mmol) in THF was treated with copper (I) iodide (7.2 mgs, 0.04 mmol) and then purged with Argon for 5 minutes. 4-iodo-1-isopropoxy-2-methylbenzene (CAS 877603-52-6) (579 mgs, 2.0 mmol), was then added followed by dichlorobis-(triphenylphosphine) palladium(II) (13.4 mgs, 0.019 mmol). The resultant mixture was heated at 80° C. overnight. The reaction mixture was filtered and the filtrate was evaporated to give the crude product. The crude product was purified on a column (MPLC) using hexane:ethyl acetate and gave Intermediate 4 (450 mgs, 76% yield).

¹H-NMR (CDCl₃, 300 MHz) δ=7.62 (s, 1H), 7.51 (d, J=8.1 Hz, 2H), 7.41 (d, J=8.1 Hz, 2H), 7.18-7.24 (m, 1H), 6.840 (d, J=9.6 Hz, 1H), 5.39 (s, 2H), 4.54-4.60 (m, 1H), 2.12 (s, 3H), 1.31 (s, 3H), 1.27 (s, 3H).

EXAMPLE 5

Intermediate 5

2-bromo-4-iodo-1-isopropoxybenzene

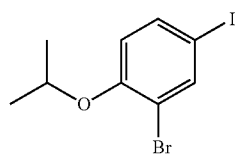

To a solution of 2-bromo-4-iodophenol (2.0 g, 6.71 mmol) in DMF (40 mL) was added K₂CO₃ (0.925 g, 6.71 mmoL) followed by 2-iodo propane (1.36 g, 8.05 mmol) at room temperature. The reaction was stirred overnight at room temperature. The solution was filtered and the filtrate evaporated to give the crude product. The crude product was purified on a column (MPLC) using hexane:ethyl acetate and gave Intermediate 5 (1.96 g, 96%)

¹H-NMR (CDCl₃, 300 MHz) δ=7.45 (d, J=12.2 Hz, 1H), 7.28 (d, J=8.5 Hz, 1H), 6.82 (d, J=9.0 Hz, 1H), 4.21-4.34 (m, 1H), 1.36 (s, 3H), 1.40 (s, 3H).

EXAMPLE 6

Compound 1

5-{[4-(1H-imidazol-1-ylmethyl)phenyl]ethynyl}-2-isopropoxybenzonitrile

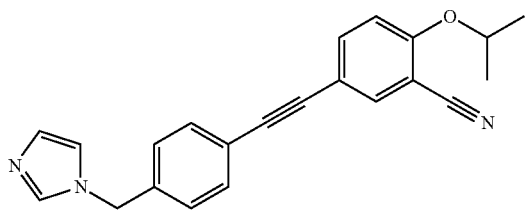 [SMILES: CC(C)Oc1ccc(C#Cc2ccc(Cn3ccnc3)cc2)cc1C#N]

Intermediate 3 (105 mgs, 0.33 mmol), imidazole (22 mgs, 0.33 mgs) and $K_2CO_3$ (140 mgs, 1.01 mmol) were stirred at reflux in $CH_3CN$ overnight. The solution was cooled to room temperature, then diluted with $CH_2Cl_2$ and washed with water. The organic phase was washed with brine (60 mL), dried over ($MgSO_4$), filtered, and concentrated under reduced pressure. Purification by column chromatography (2% MeOH in $CH_2Cl_2$) gave Compound 1.

$^1$H-NMR (CDCl$_3$, 300 MHz) δ=7.75 (s, 1H), 7.74 (s, 1H), 7.72 (d, J=8.7 Hz, 1H), 7.51 (d, J=7.8 Hz, 2H), 7.25 (d, J=8.1 Hz, 2H), 7.20 (d, J=8.7 Hz, 1H), 7.11 (s, 1H), 6.99 (s, 1H), 5.24 (s, 2H), 4.76-4.84 (m, 1H), 1.39 (s, 3H), 1.38 (s, 3H).

Compounds 2 through 7 were prepared according to the procedure in Example 6 for Compound 1 starting from the corresponding intermediates. The starting materials, the intermediates and the results are tabulated below in Table 1.

TABLE 1

| Comp No. | IUPAC name | Starting material(s) | $^1$H NMR δ (ppm) for Compound |
|---|---|---|---|
| 2 | 2-isopropoxy-5-{[4-(pyrrolidin-1-ylmethyl)phenyl]ethynyl}benzonitrile | Intermediate 1 Pyrrolidine | $^1$H-NMR (CDCl$_3$, 300 MHz) δ = 7.66 (s, 1H), 7.66 (d, J = 9 Hz, 1H), 7.44 (d, J = 8.1 Hz, 2H), 7.30 (d, J = 8.1 Hz, 2H), 6.97 (d, J = 9 Hz, 1H), 4.71-4.63 (m, 1H), 3.30 (s, 1H), 2.54 (s, 4H), 1.78 (s, 4H), 1.38 (s, 3H), 1.36 (s, 3H). |
| 3 | 1-{4-[(3-chloro-4-isopropoxyphenyl)ethynyl]-benzyl}-1H-imidazole | 4-bromo-2-chloro-1-(1-methyl ethoxy)-benzene (CAS 201849-21-0) | $^1$H-NMR (CDCl$_3$, 300 MHz) δ = 7.75 (s, 1H), 7.68 (s, 1H), 7.67 (s, 1H), 7.58 (d, J = 8.1 Hz, 2H), 7.45-7.45 (m, 1H), 7.42 (d, J = 8.1 Hz, 2H), 7.08 (s, 1H), 7.02 (d, J = 9 Hz, 1H), 5.44 (s, 2H), 4.68-4.66 (m, 1H), 1.36 (s, 3H), 1.35 (s, 3H). |
| 4 | 5-{[4-(1H-imidazol-1-ylmethyl)-2-methylphenyl]ethynyl}-2-isopropoxybenzonitrile | Intermediate 1 4-iodo-3-methyl-benzene methanol (CAS 959632-18-9) | $^1$H-NMR (CDCl$_3$, 300 MHz) δ = 7.77-7.70 (m, 2H), 7.46 (d, J = 8.1 Hz, 2H), 7.15-7.21 (m, 3H), 7.11 (d, J = 8.4 Hz, 1H), 7.04 (d, J = 8.1 Hz, 1H), 5.20 (s, 2H), 4.75-4.59 (m, 1H), 2.46 (s, 3H), 1.40 (s, 3H), 1.38 (s, 3H). |
| 5 | 5-{[2-chloro-4-(1H-imidazol-1-ylmethyl)phenyl]ethynyl}-2-isopropoxybenzonitrile | Intermediate 1 3-chloro-4-iodo-benzenemethanol (CAS 166386-60-3) | $^1$H-NMR (CDCl$_3$, 300 MHz) δ = 7.69-7.80 (m, 3H), 7.57 (d, J = 7.9 Hz, 1H), 7.42 (s, 1H), 7.35 (s, 1H) 7.11-7.26 (m, 3H), 7.02 (s, 1H), 5.26 (s, 2H), 1.40 (d, J = 6.2 Hz, 6H). |

TABLE 1-continued

| Comp No. | IUPAC name | Starting material(s) | $^1$H NMR δ (ppm) for Compound |
|---|---|---|---|
| 6 | 1-[4-(3-Methyl-4-isopropoxy-phenylethynyl)-benzyl]-1H-imidazole | 4-iodo-2-methyl-1-(1-methylethoxy)-benzene (CAS 877603-52-6) Intermediate 4 | $^1$H-NMR (CDCl$_3$, 300 MHz) δ = 7.72 (s, 1H), 7.66 (s, 1H), 7.55 (d, J = 8.1 Hz, 2H), 7.41 (d, J = 8.1 Hz, 2H), 7.20-7.30 (m, 1H), 7.07 (s, 1H), 6.90 (d, J = 9.6 Hz, 1H), 5.43 (s, 2H), 4.60-4.64 (m, 1H), 2.15 (s, 3H), 1.34 (s, 3H), 1.32 (s, 3H). |
| 7 | 1-[4-(3-Bromo-4-isopropoxy-phenylethynyl)-benzyl]-1H-imidazole | Intermediate 5 | $^1$H-NMR (CDCl$_3$, 300 MHz) δ = 7.75 (s, 1H), 7.68 (s, 1H), 7.67 (s, 1H), 7.58 (d, J = 8.1 Hz, 2H), 7.45-7.45 (m, 1H), 7.42 (d, J = 8.1 Hz, 2H), 7.08 (s, 1H), 7.02 (d, J = 9 Hz, 1H), 5.44 (s, 2H), 4.68-4.66 (m, 1H), 1.36 (s, 3H), 1.35 (s, 3H). |

Biological Data

Novel compounds were synthesized and tested for S1P1 activity using the GTP γ$^{35}$S binding assay. These compounds may be assessed for their ability to activate or block activation of the human S1P1 receptor in cells stably expressing the S1P1 receptor. GTP γ$^{35}$S binding was measured in the medium containing (mM) HEPES 25, pH 7.4, MgCl$_2$ 10, NaCl 100, dithiothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH 7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method, the results are presented in Table 2. In case of antagonist assay, the reaction mixture contained 10 nM S1P in the presence of test antagonist at concentrations ranging from 0.08 to 5000 nM.

TABLE 2

| IUPAC name | S1P1 EC$_{50}$ nM | % stimulation |
|---|---|---|
| 5-{[4-(1H-imidazol-1-ylmethyl)phenyl]ethynyl}-2-isopropoxybenzonitrile | 6.3 | 0.67 |
| 5-{[4-(1H-imidazol-1-ylmethyl)-2-methylphenyl]ethynyl}-2-isopropoxybenzonitrile | 3.1 | 0.70 |
| 1-[4-(3-Chloro-4-isopropoxy-phenylethynyl)-benzyl]-1H-imidazole | 14.7 | 0.81 |
| 2-isopropoxy-5-{[4-(pyrrolidin-1-ylmethyl)phenyl]ethynyl}benzonitrile | 365 | 1.10 |
| 5-{[2-chloro-4-(1H-imidazol-1-ylmethyl)phenyl]ethynyl}-2-isopropoxybenzonitrile | 7.52 | 1.08 |

Activity potency: S1P1 receptor from GTP γ$^{35}$S: nM, (EC$_{50}$), % stimulation,

What is claimed is:

1. A compound having Formula I, its individual enantiomers, individual diastereoisomers, individual tautomers or a pharmaceutically acceptable salt thereof,

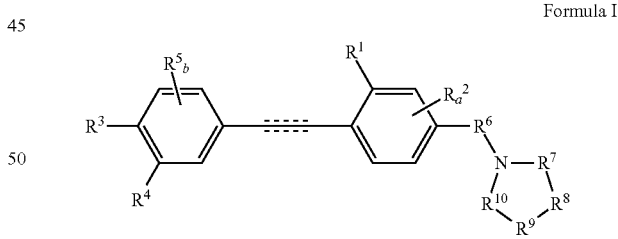

Formula I wherein:

"= = = = =" represents a triple bond "—C≡C—";

R$^1$ is H, halogen, —OC$_{1-3}$ alkyl, C$_{1-8}$ alkyl, CN, C(O)R$^{11}$, C$_{3-8}$ cycloalkyl, C$_{3-10}$ cycloalkenyl, C$_{6-10}$ aryl, heterocycle, NR$^{12}$R$^{13}$ or hydroxyl;

R$^3$ is H, halogen, —OC$_{1-3}$ alkyl, C$_{1-8}$alkyl, CN, C$_{3-8}$ cycloalkyl, C$_{3-10}$ cycloalkenyl, C$_{6-10}$ aryl, heterocycle, NR$^{12}$R$^{13}$ or hydroxyl;

R$^4$ is halogen, —OC$_{1-3}$ alkyl, C$_{1-8}$alkyl, CN, C(O)R$^{11}$, C$_{3-8}$ cycloalkyl, C$_{3-10}$ cycloalkenyl, C$_{6-10}$ aryl, heterocycle, NR$^{12}$R$^{13}$ or hydroxyl;

R$^6$ is CR$^{16}$R$^{17}$;

R$^7$ forms together with R$^8$ a HC═N double bond;

R⁹ forms together with R¹⁰ a HC=CH double bond;
R¹¹ is H, $C_{3-8}$ cycloalkyl, $C_{3-10}$ cycloalkenyl, $C_{6-10}$ aryl, heterocycle, or $C_{1-5}$ alkyl;
R¹² is H, $C_{3-8}$ cycloalkyl, $C_{3-10}$ cycloalkenyl, $C_{6-10}$ aryl, heterocycle, or $C_{1-5}$ alkyl;
R¹³ is H, $C_{3-8}$ cycloalkyl, $C_{3-10}$ cycloalkenyl, $C_{6-10}$ aryl, heterocycle, or $C_{1-5}$ alkyl;
R¹⁶ is H, halogen or $C_{1-8}$alkyl;
R¹⁷ is H, halogen or $C_{1-8}$alkyl;
a is 0; and
b is 0.

2. A compound according to claim 1, wherein:
" ====== " represents a triple bond "—C≡C";
R¹ is H, halogen or $C_{1-8}$alkyl;
R³ is —$OC_{1-3}$ alkyl;
R⁴ is halogen, $C_{1-8}$alkyl or CN;
R⁶ is CR¹⁶R¹⁷;
R⁷ forms together with R⁸ a HC=N double bond;
R⁹ forms together with R¹⁰ a HC=CH double bond;
R¹⁶ is H;
R¹⁷ is H;
a is 0; and
b is 0.

3. A compound according to claim 2, wherein:
R³ is —O(iso-propyl).

4. A compound according to claim 1 selected from:
5-{[4-(1H-imidazol-1-ylmethyl)phenyl]ethynyl}-2-isopropoxybenzonitrile;
5-{[4-(1H-imidazol-1-ylmethyl)-2-methylphenyl]ethynyl}-2-isopropoxybenzonitrile;
1-[4-(3-Chloro-4-isopropoxy-phenylethynyl)-benzyl]-1H-imidazole;
5-{[2-chloro-4-(1H-imidazol-1-ylmethyl)phenyl]ethynyl}-2-isopropoxybenzonitrile;
1-{4-[(3-bromo-4-isopropoxyphenyl)ethynyl]benzyl}-1H-imidazole; and
1-[4-(3-Methyl-4-isopropoxy-phenylethynyl)-benzyl]-1H-imidazole.

5. A pharmaceutical composition comprising as active ingredient a therapeutically effective amount of a compound according to claim 1 and a pharmaceutically acceptable adjuvant, diluents or carrier.

6. A pharmaceutical composition according to claim 5 wherein the compound is selected from:
5-{[4-(1H-imidazol-1-ylmethyl)phenyl]ethynyl}-2-isopropoxybenzonitrile;
5-{[4-(1H-imidazol-1-ylmethyl)-2-methylphenyl]ethynyl}-2-isopropoxybenzonitrile;
1-[4-(3-Chloro-4-isopropoxy-phenylethynyl)-benzyl]-1H-imidazole;
5-{[2-chloro-4-(1H-imidazol-1-ylmethyl)phenyl]ethynyl}-2-isopropoxybenzonitrile;
1-{4-[(3-bromo-4-isopropoxyphenyl)ethynyl]benzyl}-1H-imidazole; and
1-[4-(3-Methyl-4-isopropoxy-phenylethynyl)-benzyl]-1H-imidazole.

* * * * *